Figure 1:
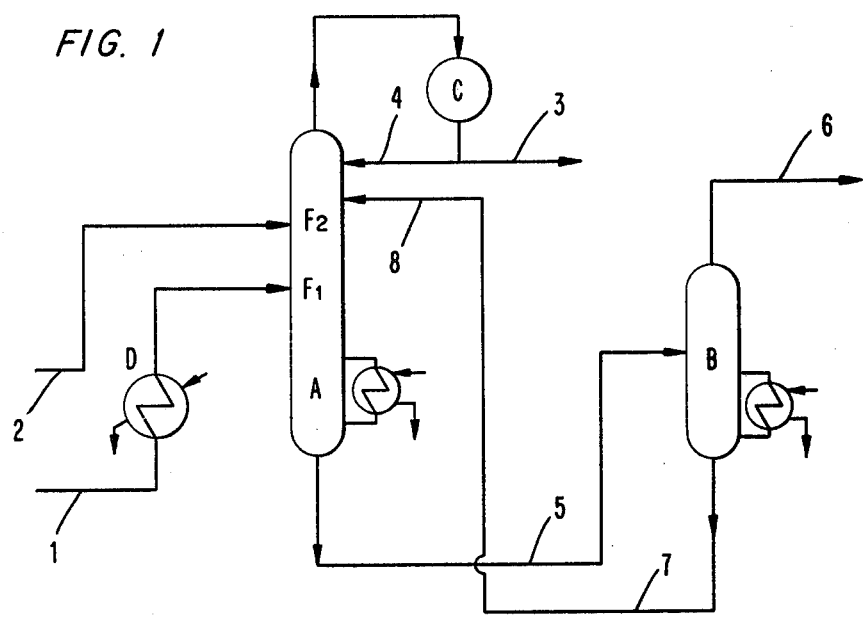

United States Patent [19]

Ogura

[11] 4,421,607
[45] Dec. 20, 1983

[54] PROCESS FOR EXTRACTIVE DISTILLATION OF PLURAL HYDROCARBON MIXTURES

[75] Inventor: Shunichiro Ogura, Tokyo, Japan

[73] Assignee: Nippon Zeon Co. Ltd., Tokyo, Japan

[21] Appl. No.: 463,049

[22] Filed: Feb. 1, 1983

[30] Foreign Application Priority Data

Feb. 2, 1982 [JP] Japan ................................. 57-15329

[51] Int. Cl.³ .......................... B01D 3/40; C07C 7/08
[52] U.S. Cl. ........................................ 203/60; 203/58; 203/DIG. 9; 585/807; 585/808; 585/809; 585/810
[58] Field of Search .................... 203/60, 58, DIG. 9, 203/50, 51, 53–57, 59, 61–67, 99; 585/807–810, 834, 860, 865

[56] References Cited

U.S. PATENT DOCUMENTS 3,050,448  8/1962  Fenske et al. ...................... 585/809
3,422,163  1/1969  Asselin ............................... 585/807
3,436,436  4/1969  Takao et al. ........................... 203/60
3,654,094  4/1972  Yamagishi et al. ........... 203/DIG. 9
3,798,132  3/1974  Sarno .................................. 585/865
4,070,408  1/1978  Vickers ........................... 203/DIG. 9
4,158,611  6/1979  Cooke ............................ 203/DIG. 9

Primary Examiner—Wilbur L. Bascomb, Jr.
Attorney, Agent, or Firm—Sherman & Shalloway

[57] ABSTRACT

A process of extractive distillation for separating components easily soluble in a polar solvent from at least two hydrocarbon mixtures having different contents of the easily soluble components by extractive distillation using said polar solvent, which comprises feeding a hydrocarbon mixture containing a larger amount of the easily soluble components, as a gas, into the middle or lower portion of an extractive distillation column, feeding a hydrocarbon mixture containing a smaller amount of the easily soluble components, as a liquid, to the upper portion of the extractive distillation column, and subjecting them to extractive distillation.

5 Claims, 2 Drawing Figures

PROCESS FOR EXTRACTIVE DISTILLATION OF PLURAL HYDROCARBON MIXTURES

This invention relates to an improvement in a process for separating components easily soluble in polar solvents from at least two hydrocarbon mixtures having different contents of the soluble components by extractive distillation with polar solvents.

It is well known to subject a hydrocarbon mixture containing paraffinic, olefinic and diolefinic hydrocarbons to extractive distillation with a polar solvent thereby separating these hydrocarbon components. In the extractive distillation, paraffinic hydrocarbons difficulty soluble in the polar solvent are usually discharged as a raffinate from the top of a distillation column, and diolefinic hydrocarbons easily soluble in the polar solvent are usually discharged as an extract from the bottom of the column together with the solvent. Olefinic hydrocarbons are discharged from the top or bottom of the column depending upon the operating conditions for the extractive distillation. For example, Japanese Patent Publication No. 17407/1970 discloses a process for separating 1,3-butadiene by extractive distillation using dimethylformamide as a solvent from a hydrocarbon fraction composed mainly of $C_4$ hydrocarbons containing 1,3-butadiene obtained during the cracking of naphtha. According to this process, paraffinic hydrocarbons (isobutane and n-butane) and olefinic hydrocarbons (butene-1, isobutene, trans-butene-2 and cis-butene-2) are obtained from the top of the distillation column, and a conjugated diolefinic hydrocarbon (1,3-butadiene), from the bottom of the column.

Much interest has recently been aroused in a $C_4$ hydrocarbon fraction because the separation of the $C_4$ components can give 1,3-butadiene as a material for synthetic rubbers, isobutene and maleic anhydride as materials for methyl methacrylate, and n-butene as a material for dehydrogenated butadiene.

It is an object of this invention therefore to separate olefinic hydrocarbons and/or diolefinic hydrocabons with good efficiency at low cost by feeding at least two hydrocarbon mixtures having markedly different contents of the olefinic hydrocarbons and/or the diolefinic hydrocarbons into a single extractive distillation column.

The hydrocarbon mixtures to be used in this invention usually denote mixtures of hydrocarbons having 3 to 6 carbon atoms formed by an apparatus for steam cracking of naphtha and/or butane, an apparatus for catalytic cracking of petroleum (e.g., an FCC apparatus), an apparatus for thermally decomposing residual heavy oils (e.g., coker), etc., but is not limited to these specific materials.

The present inventor assiduously studied a process for separating components from hydrocarbon mixtures having a similar composition to that exemplified in Table 1 below by feeding them into an extractive distillation apparatus using a polar solvent, especially dimethylformamide, and consequently found that when easily soluble hydrocarbons are separated from at least two hydrocarbon mixtures having markedly different compositions by a method which comprises feeding a hydrocarbon mixture containing a larger amount of components easily soluble in a polar solvent, as a gas, into the middle or lower portion of an extractive distillation column and a hydrocarbon mixture containing a smaller amount of the easily soluble components, as a liquid, to the upper portion of the extractive distillation column, and subjecting them to extractive distillation, these components can be separated with much better efficiency and more economically than by using a method which comprises feeding at least two hydrocarbon mixtures as a single mixture.

TABLE 1

(Composition of a $C_4$ hydrocarbon fraction and the solubilities of the hydrocarbon components in dimethylformamide)

| Component | Boiling point (°C.) | Composition of $C_4$ hydrocarbon fraction (wt. %) | | | | Solubility in dimethyl-formamide (Vol/Vol/1 atm.) |
|---|---|---|---|---|---|---|
| | | Catalytic cracking | Steam cracking (naphtha as material) | Steam cracking (n-butane as material) | Coker | |
| Propane | −42.1 | 1.8 | 0.1 | — | — | 4.0 (25° C.) |
| Propylene | −47.7 | 1.0 | 0.1 | — | — | 8.2 (25° C.) |
| iso-Butane | −11.5 | 31.6 | 2.0 | 7.0 | 11.0 | 9.2 (20° C.) |
| n-Butane | −0.5 | 7.4 | 7.0 | 47.0 | 35.0 | 16.5 (20° C.) |
| iso-Butene | −6.6 | 20.0 | 25.0 | 2.0 | 7.2 | 28.0 (20° C.) |
| Butene-1 | −6.5 | 17.4 | 12.0 | 17.5 | 22.8 | 24.6 (20° C.) |
| trans-Butene-2 | +0.3 | 13.9 | 5.0 | 5.5 | 12.0 | 35.5 (20° C.) |
| cis-Butene-2 | +3.7 | 6.7 | 4.5 | 4.0 | 6.0 | 51 (20° C.) |
| 1,3-Butadiene | −4.7 | 0.1 | 43.0 | 16.0 | 6.0 | 83.4 (20° C.) |
| Methylacetylene | −23.2 | — | 0.05 | 0.05 | — | 85 (20° C.) |
| 1,2-Butadiene | +10.3 | — | 0.45 | 0.45 | — | 160 (20° C.) |
| Vinylacetylene | — | — | 0.6 | 0.30 | — | 350 (20° C.) |
| $C_5$ | — | 0.1 | 0.2 | 0.2 | — | — |
| | | 100.0 | 100.0 | 100.0 | 100.0 | |

The extractive distillation process of this invention is applied to the separation of paraffinic hydrocarbons and olefinic hydrocarbons from at least two hydrocarbon mixtures containing $C_3$–$C_6$ paraffinic hydrocarbons and $C_3$–$C_6$ olefinic hydrocarbons and having different contents of the olefinic hydrocarbons which are easily soluble in polar solvents.

The extractive distillation process of this invention is also applicable to the separation of paraffinic hydrocarbons and a mixture of olefinic and diolefinic hydrocarbons, or diolefinic hydrocarbons and a mixture of paraffinic and olefinic hydrocarbons, from at least two hydrocarbon mixtures containing $C_3$–$C_6$ paraffinic hydrocarbons, $C_3$–$C_6$ olefinic hydrocarbons, and $C_4$–$C_6$ diolefinic hydrocarbons and having different contents of components easily soluble in polar solvents.

In the present invention, polar solvents usually employed as solvents for the extractive distillation of 1,3-butadiene from a $C_4$ hydrocarbon fraction can be used.

Examples include N-alkylated lower fatty acid amides, furfural, N-methylpyrrolidone, formylmorpholine, β-methoxypropionitrile and acetonitrile. Illustrative of the N-alkylated lower fatty acid amides are dimethylformamide, diethylformamide and dimethylacetamide. These solvents are suitable solvents for use in this invention because in an anhydrous condition, they have an excellent solubility, an excellent relative volatility and a moderate boiling point. Table 2 below summarizes the relative volatilities of $C_4$ hydrocarbons in various polar solvents. Dimethylformamide is an especially preferred polar solvent for use in this invention because it has a suitable boiling point and an excellent relative volatility.

These polar solvents may be used singly or as a mixture of at least two. To adjust the boiling point of the polar solvent, it may be mixed with a suitable amount of water, methanol, etc. It may also be used in combination with a polymerization inhibitor for inhibiting polymerization of diolefinic and/or acetylenic hydrocarbons, an antioxidant, a defoamer, etc. Various compounds having the property of inhibiting polymerization and/or transferring chains can be used as the polymerization inhibitor. In particular, it is preferred to use t-butylcatechol, sulfur, sodium nitrite, furfural, benzaldehyde, aromatic nitro compounds, etc. either singly or as a mixture of two or more.

TABLE 2

Relative volatilities of various polar solvents (data at 50° C. with infinite dilution)

| Solvent<br>Boiling point (°C.) | | Dimethyl-<br>formamide<br>153 | Diethyl-<br>formamide<br>177.50 | N—methyl-<br>pyrrolidone<br>202 |
|---|---|---|---|---|
| $C_4$ | iso-Butane | 5.3 | 5.2 | 7.25 |
| Hydro- | n-Butane | 3.8 | 3.6 | 4.30 |
| carbons | Butene-1 | 2.4 | 2.3 | 2.60 |
| | trans-Butene-2 | 1.9 | 1.8 | 2.00 |
| | cis-Butene-2 | 1.7 | 1.5 | 1.63 |
| | 1,3-Butadiene | 1.0 | 1.0 | 1.00 |
| | Methylacety-<br>lene | 0.95 | 0.96 | 0.96 |
| | 1,2-Butadiene | 0.53 | 0.55 | 0.53 |
| | Ethylacetylene | 0.40 | 0.43 | 0.41 |
| | Vinylacetylene | 0.24 | 0.29 | 0.18 |

The process of this invention will now be more specifically described by the accompanying drawings and the following Examples and Control Examples.

Figure 2:
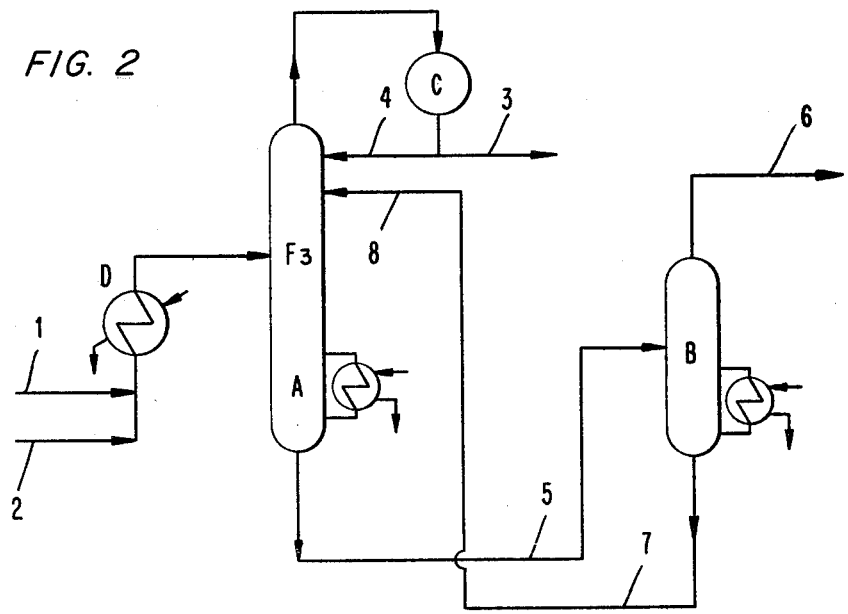

In the accompanying drawings,

FIG. 1 is a diagram illustrating a preferred embodiment in the process of this invention, and FIG. 2 is a diagram illustrating a conventional process.

Two mixtures containing paraffinic, olefinic and diolefinic hydrocarbons are used as starting materials. One mixture containing a larger amount of olefinic and diolefinic hydrocarbons which are easily soluble in polar solvents (high-concentration material) is fed through a line 1 into a vaporizer D where it is gasified. The gas is then sent to a middle tray ($F_1$) in an extractive distillation column A containing 100 trays. The other mixture containing a smaller amount of the easily-soluble hydrocarbons (low-concentration material) is fed in the liquid state into a tray $R_2$ ten to several tens of trays above $F_1$ through a line 2. Thus, the mixtures are subjected to extractive distillation.

A polar solvent is fed into that part of the column A which is several trays below its top through a line 8. From the top of the column, paraffinic and/or olefinic hydrocarbons which are a difficulty soluble component are discharged in the gaseous state, condensed and liquefied in a condenser C, and withdrawn through a line 3. The reflux liquid is returned to the top of the column through a line 4. The extractive distillation column can be operated at a column bottom temperature of 80° to 200° C. and a column inside pressure of 1 to 20 atmospheres. From the bottom of the column, olefinic and/or diolefinic hydrocarbons are withdrawn together with the polar solvent, fed to a stripping column B at that part of the column B which is several trays below its top, and thus separated into the hydrocarbons and the polar solvent. Usually, the stripping column B can be operated at a column inside pressure of 0.5 to 4 atmospheres and a column bottom temperature corresponding to the boiling point of the solvent at the above pressure. From the top of the stripping column, olefinic and/or diolefinic hydrocarbons are obtained through a line 6. From the bottom of the stripping column, only the solvent is withdrawn through a line 7, and recycled to the extractive distillation column A through the line 8.

According to the process shown in FIG. 2, a high-concentration material from a line 1 and a low-concentration material from a line 2 are mixed upstream of a vaporizer D and then gasified in the vaporizer D. The gas is fed into a middle tray ($F_3$) of a column A, and thereafter, the same operation as in FIG. 1 is carried out.

EXAMPLE 1

By using the apparatus illustrated in FIG. 1, the following operation was performed.

One hundred kilograms/hour of a starting material 1 (high-concentration material) shown in Table 3 was gasified in vaporizer D and fed into a middle tray ($F_1$) of extractive distillation column A containing 100 trays through line 1. In the meantime, a starting material 2 (low-concentration material) shown in Table 3 was fed in the liquid state into a tray ($F_2$) 20 trays above the tray $F_1$ through line 2 at a rate of 34 kg/hour. As a polar solvent, 800 kg/hour of anhydrous dimethylformamide was fed into the column A at that part of the column A which was several trays below its top. The reflux liquid was sent to the top of the column at a rate of 84 kg/hour. The extractive distillation column was operated while maintaining the pressure of the top of the column at 3.5 kg/cm$^2$-G, the temperature of its top at 45° C., and the temperature of its bottom at 135° C. From the top of the extractive distillation column A, a mixture of paraffinic and olefinic hydrocarbons having the composition shown in Table 3 was obtained through line 3 at a rate of 86.5 kg/hour. From the top of stripping column B, a gaseous mixture consisting mainly of diolefinic hydrocarbons having the composition shown in Table 3 was obtained at a rate of 47.5 kg/hour. The total amount of steam required in the extractive distillation column A, the stripping column B and the vaporizer D was 135 kg/hour.

TABLE 3

| Components | Material 1<br>from line<br>1 (high-<br>concentra-<br>tion ma-<br>terial) | Material 2<br>from line<br>2 (low-<br>concentra-<br>tion ma-<br>terial) | Paraffinic<br>and olefinic<br>hydrocarbons<br>through<br>line 3 | Diolefinic<br>hydro-<br>carbons<br>through<br>line 6 |
|---|---|---|---|---|
| iso-Butane | 2.2% | 11.0% | 6.9% | — |
| n-Butane | 7.0 | 35.0 | 21.7 | — |
| iso-Butene | 25.0 | 7.0 | 31.8 | — |
| Butene-1 | 12.0 | 22.0 | 22.9 | — |

TABLE 3-continued

| Components | Material 1 from line 1 (high-concentration material) | Material 2 from line 2 (low-concentration material) | Paraffinic and olefinic hydrocarbons through line 3 | Diolefinic hydrocarbons through line 6 |
| --- | --- | --- | --- | --- |
| trans-Butene-2 | 5.0 | 12.0 | 10.4 | 0.1% |
| cis-Butene-2 | 4.5 | 6.0 | 6.0 | 2.9 |
| 1,3-Butadiene | 43.0 | 6.0 | 0.3 | 94.25 |
| Methylacetylene | 0.05 | — | — | 0.1 |
| 1,2-Butadiene | 0.45 | — | — | 0.95 |
| Vinylacetylene | 0.6 | — | — | 1.3 |
| $C_5$ | 0.2 | — | — | 0.4 |
|  | 100.0 | 100.0 | 100.0 | 100.0 |

The anhydrous dimethylformamide used as a polar solvent in this example contained 0.1% by weight of nitrobenzene and 0.05% by weight of sodium nitrite.

CONTROL EXAMPLE 1

By using the apparatus illustrated in FIG. 2, the following operation was performed.

One hundred kilograms/hour of a starting material 1 (high-concentration material) having the composition shown in Table 3 were combined upstream of vaporizer D. The resulting mixture (see Table 4 for its composition) was gasified by vaporizer D, and fed into a middle tray ($F_3$) of extractive distillation column A having 100 trays. Anhydrous dimethylformamide (the same as that used in Example 1) as a polar solvent was fed into that part of the column A which was several trays below its top at a rate of 1040 kg/hour. The reflux liquid was fed from the top of the column at a rate of 118 kg/hour. The extractive distillation column A was operated while maintaining the pressure of the top of the column at 3.5 kg/cm²-G, the temperature of its top at 45° C. and the temperature of its bottom at 145° C. From the top of the extractive distillation column A, 86.5 kg/hour of a mixture of paraffinic and olefinic hydrocarbons having the composition shown in Table 4 was obtained through line 3. From the top of the stripping column B, 47.5 kg/hour of a gaseous mixture consisting mainly of diolefinic hydrocarbons having the composition shown in Table 4 was obtained through line 6.

TABLE 4

| Components | Material | Paraffinic and olefinic hydrocarbons from line 3 | Diolefinic hydrocarbons from line 6 |
| --- | --- | --- | --- |
| iso-Butane | 4.4 | 6.9 | — |
| n-Butane | 14.1 | 21.7 | — |
| iso-Butene | 20.5 | 31.9 | — |
| Butene-1 | 14.7 | 22.9 | — |
| trans-Butene-2 | 6.8 | 10.4 | 0.1 |
| cis-Butene-2 | 4.9 | 5.9 | 3.0 |
| 1,3-Butadiene | 33.62 | 0.3 | 94.1 |
| Methylacetylene | 0.04 | — | 0.1 |
| 1,2-Butadiene | 0.34 | — | 1.0 |
| Vinylacetylene | 0.45 | — | 1.3 |
| $C_5$ | 0.15 | — | 0.4 |
|  | 100.0 | 100.0 | 100.0 |

A comparison of Table 3 with Table 4 shows that the compositions of the gases from the top of the distillation column and the top of the stripping column in Control Example 1 are much the same as those in Example 1. But in Control Example 1, the total amount of steam required in the extractive distillation column A, the stripping column B and the vaporizer D was 183 kg/hour. In other words, in Control Example 1, the amounts of the polar solvent, the reflux liquid and steam required were larger than those in Example 1 by 30%, 40%, and 36%, respectively.

EXAMPLE 2

By using the apparatus illustrated in FIG. 1, the following operation was performed for the separation of two paraffinic-olefinic hydrocarbon mixtures having different compositions, in which the olefinic hydrocarbons were an easily soluble component.

A starting material 3 (high-concentration material) indicated in Table 5 was gasified in vaporizer D at a rate of 66.7 kg/hour, and fed into a middle tray ($F_1$) of extractive distillation column A having 100 trays through line 1. In the meantime, a material 4 (low-concentration material) indicated in Table 5 was fed in the liquid state into a tray ($F_2$) 25 trays above the tray $F_1$ through line 2 at a rate of 33.3 kg/hour. Anhydrous dimethylformamide (the same as that used in Example 1) as a polar solvent was fed into that part of the column which was several trays below its top at a rate of 900 kg/hour. The reflux liquid was fed to the top of the column at a rate of 49 kg/hour. The extractive distillation column A was operated while maintaining the pressure of the top of the column at 4.0 kg/cm²-G, the temperature of its top at 45° C. and the temperature of its bottom at 135° C. From the top of the column A, a paraffinic hydrocabon mixture having the composition shown in Table 5, was obtained through line 3 at a rate of 41 kg/hour. From the top of the stripping column B, an olefinic hydrocarbon mixture having the composition shown in Table 5 was obtained at a rate of 59 kg/hour through line 6. The total amount of steam required in the extractive distillation column A, the stripping column B and the vaporizer D was 145 kg/hour.

TABLE 5

| Components | Material 3 from line 1 (high-concentration material) | Material 4 from line 2 (low-concentration material) | Paraffinic hydrocarbons from line 3 | Olefinic hydrocarbons from line 6 |
| --- | --- | --- | --- | --- |
| iso-Butane | 7.5% | 24.80% | 32.3% | 0.0% |
| n-Butane | 19.0 | 45.13 | 63.15 | 3.1 |
| iso-Butene | 0.1 | 0.03 | 0.0 | 0.1 |
| Butene-1 | 58.9 | 9.90 | 4.5 | 69.0 |
| trans-Butene-2 | 10.3 | 13.30 | 0.05 | 19.2 |
| cis-Butene-2 | 4.0 | 6.84 | 0.0 | 8.4 |
| $C_5$ | 0.2 | 0.0 | 0.0 | 0.2 |
|  | 100.0 | 100.0 | 100.0 | 100.0 |

CONTROL EXAMPLE 2

By using the apparatus illustrated in FIG. 2, the following operation was performed.

66.7 kg/hour of a starting material 3 (high-concentration material) having the composition shown in Table 5 and 33.3 kg/hour of a starting material 4 (low-concentration material) having the composition shown in Table 5 were combined upstream of vaporizer D. The resulting mixture (see Table 6 for its composition) was gasified by vaporizer D and fed into a middle tray (F₃) of extractive distillation column A having 100 trays. Anhydrous dimethylformamide (the same as that used in Example 1) as a polar solvent was fed into that part of the column A which was several trays below its top at a rate of 1125 kg/hour. The reflux liquid was fed to the top of the column A at a rate of 82 kg/hour. The column A was operated while maintaining the pressure of the top of the column at 3.0 kg/cm²-G, the temperature of its top at 45° C., and the temperature of its bottom at 145° C. From the top of the extractive distillation column A, 41 kg/hour of a paraffinic hydrocarbon mixture having the composition shown in Table 6 was obtained through line 3. From the top of the stripping column B, 59 kg/hour of an olefinic hydrocarbon mixture having the composition shown in Table 6 was obtained through line 6.

TABLE 6

| Components | Starting material | Paraffinic hydrocarbons from line 3 | Olefinic hydrocarbons from line 6 |
|---|---|---|---|
| iso-Butane | 13.27% | 32.3% | 0.0% |
| n-Butane | 27.71 | 63.0 | 3.2 |
| iso-Butene | 0.08 | 0.0 | 0.1 |
| Butene-1 | 42.56 | 4.6 | 69.0 |
| trans-Butene-2 | 11.30 | 0.06 | 19.1 |
| cis-Butene-2 | 4.95 | 0.0 | 8.4 |
| C₅ | 0.13 | 0.0 | 0.2 |
| | 100.0 | 100.0 | 100.0 |

A comparison of Table 6 with Table 5 shows that the compositions of the gases from the tops of the extractive distillation column and the stripping column were much the same as those in Example 2. But the total amount of steam required in the extractive distillation column A, the stripping column B and the vaporizer D in Control Example 2 was 189 kg/hour. In other words, in Control Example 2, the amounts of the polar solvent, the reflux liquid and steam required were larger than those in Example 2 by 25%, 67% and 30%, respectively.

What is claimed is:

1. A process of extractive distillation for separating components easily soluble in a polar solvent from at least two hydrocarbon mixtures having different contents of the easily soluble components by extractive distillation using said polar solvent, which comprises feeding a hydrocarbon mixture containing a larger amount of the easily soluble components, as a gas, into the middle or lower portion of an extractive distillation column, feeding a hydrocarbon mixture containing a smaller amount of the easily soluble components, as a liquid, to the upper portion of the extractive distillation column, and subjecting them to extractive distillation.

2. The process of claim 1 wherein olefinic hydrocarbons are separated from at least two hydrocarbon mixtures containing paraffinic hydrocarbons and olefinic hydrocarbons and having different contents of the olefinic hydrocarbons which are easily soluble in the polar solvent.

3. The process of claim 2 wherein the polar solvent is dimethylformamide.

4. The process of claim 1 wherein diolefinic hydrocarbons are separated from at least two hydrocarbon mixtures containing paraffinic hydrocarbons, olefinic hydrocarbons and diolefinic hydrocarbons and having different contents of the diolefinic hydrocarbons which are easily soluble in the polar solvent.

5. The process of claim 4 wherein the polar solvent is dimethylformamide.

* * * * *